United States Patent
Mengato

(10) Patent No.: US 6,945,252 B2
(45) Date of Patent: Sep. 20, 2005

(54) SURGICAL HAND SUPPORT

(76) Inventor: Richard A. Mengato, 2969 Kalakaua Ave., No. 801, Honolulu, HI (US) 96815

( * ) Notice: Subject to any disclaimer, the term of this patent is extended or adjusted under 35 U.S.C. 154(b) by 0 days.

(21) Appl. No.: 10/752,784

(22) Filed: Jan. 5, 2004

(65) Prior Publication Data
US 2005/0145255 A1 Jul. 7, 2005

(51) Int. Cl.⁷ .............................................. A61F 5/37
(52) U.S. Cl. ...................... 128/878; 128/879; 128/880
(58) Field of Search ............................... 128/778, 779, 128/780, 878, 879, 880; 602/20, 21, 22

(56) References Cited

U.S. PATENT DOCUMENTS

| | | | | |
|---|---|---|---|---|
| 1,298,529 A | * | 3/1919 | Maddox | 602/21 |
| 1,708,757 A | * | 4/1929 | Freileweh | 602/20 |
| 3,815,588 A | * | 6/1974 | Klausner | 602/4 |
| 4,082,257 A | | 4/1978 | Strickland | |
| 5,058,576 A | | 10/1991 | Grim et al. | |
| 5,121,743 A | | 6/1992 | Bishop | |
| 5,140,998 A | | 8/1992 | Vickers | |
| D371,845 S | * | 7/1996 | Varn | D24/190 |
| 6,422,975 B1 | * | 7/2002 | Chermak | 482/46 |

* cited by examiner

Primary Examiner—Henry Bennett
Assistant Examiner—Camtu Nguyen
(74) Attorney, Agent, or Firm—Carothers & Carothers

(57) ABSTRACT

A surgical hand support for performing surgical procedures on the volar side of the human thumb. The support includes an elongate forearm support plate with a hand support plate and a thumb support plate extending from this forearm support plate. The hand support plate and thumb support plate are dimensioned for respectively engaging the back of an individual's hand and thumb. The hand support plate extends upwardly from a wrist bend on the forward edge of the forearm support plate at an obtuse angle. The thumb support plate extends upwardly from a side edge of the forearm plate adjacent the wrist bend at an obtuse angle and the thumb support plate also extends forward from the side edge of the forearm plate at an obtuse angle and adjustable straps are provided for securing the forearm to the forearm plate, the hand to the hand plate and the thumb to the thumb plate whereby the volar side of the thumb is suitably presented for surgery.

5 Claims, 3 Drawing Sheets

SURGICAL HAND SUPPORT

BACKGROUND OF THE INVENTION

This invention relates generally to medical devices, and more particularly to a surgical hand support for performing surgical procedures on the volar side of the human thumb.

Surgical procedures on the volar, or palm, side of the thumb, are relatively common and include effective procedures such as A1 pulley (trigger thumb) release and urgent or relatively urgent reparative procedures following trauma such as for repair of flexor tendons or digital nerves or arteries. The contour of the human hand and thumb are such that with the hand laying flat, facing palm up, the thumb sits in a relatively pronated position, that is, rotated such that it's volar surface faces somewhat towards the radially side of the index finger rather than facing directly upward. This position facilitates pinching activity between the thumb and index finger and other digits, as well as use of the thumb during gripping activities. For many surgical procedures on the thumb, however, this natural position of the thumb relative to the hand makes it difficult to maintain the thumb in a position that allows appropriate access and visualization of the areas of interest on the volar side of the thumb by simple positioning of the hand in the usual manner, i.e., with the hand lying flat with the palm facing upward.

Usually, an assistant or the surgeon must manually hold the thumb and hand in such a way as to present or expose the volar side of the thumb directly to the operating surgeon and maintain the thumb in a stable position to be worked upon. Normally, retractors must also be manually held within the surgical wound to allow visualization of the deeper structures by the surgeon. For even a relatively simple procedure such as an A1 pulley release of the thumb, three or four retractors may need to be held simultaneously along with the holding or maintaining of the thumb itself in an appropriate position.

If limited assistance is available, such as is the situation with a surgical case being done by a single surgeon with a single scrub technician or scrub nurse assisting, holding all of the necessary objects (thumb and retractors) can be extremely awkward, cumbersome or impossible with the available number of hands. If the scrub assistant has one or both hands involved holding the thumb and hand, he or she may not be able to hold necessary retractors or reach for and hand to the surgeon instruments needed to perform the operation.

For procedures being done under magnification, particularly under an operating microscope, manually holding the thumb may cause an unacceptable amount of shaking for repairing a nerve or artery even with a steady handed assistant. This can make the procedures more difficult and more time consuming. In addition, the very expensive rate for the operating room in this instance can cause significant cost increases for such surgical procedures.

A principal object of the present invention to provide a table or support which secures the hand and thumb in the appropriate position for volar surgery to the thumb without requiring manual holding by an assistant, and which will steadily retain the hand and thumb in position while doing fine microscopic procedures.

SUMMARY OF THE INVENTION

The surgical hand support of the present invention is comprised of a rigid support including an elongate forearm support plate with a hand support plate and a thumb support plate extending from the forearm support plate. The hand support plate and the thumb support plate are dimensioned for respectively engaging the back of an individual's hand and the thumb of the hand.

The hand support plate extends upwardly from a wrist bend on the forward edge of the forearm support plate at an obtuse angle. The thumb support plate extends upwardly from a side edge of the forearm support plate adjacent the wrist bend at an obtuse angle. The thumb support plate also extends forwardly from the side edge at an obtuse angle. Accordingly, the thumb is abducted in the plane of the palm and out of the plane of the palm with the net result of presenting the volar surface of the thumb to the operating surgeon in a suitable position to perform typical surgical procedures in that region. The forearm, hand and thumb are secured with straps to the respective plates. The adjustable straps may be secured with hook and loop fasteners and may be selectively positioned on the respective plates by providing multiple selections for positioning the straps, such as with the use of multiple slot positions on the respective plates for receiving the straps at different positions therealong.

BRIEF DESCRIPTION OF THE DRAWINGS

Other objects and advantages appear hereinafter in the following description and claims. The accompanying drawings show, for the purpose of exemplification, without limiting the invention or appended claims, certain practical embodiments of the present invention wherein:

DETAILED DESCRIPTION OF A PREFERRED EMBODIMENT

Figure 1:
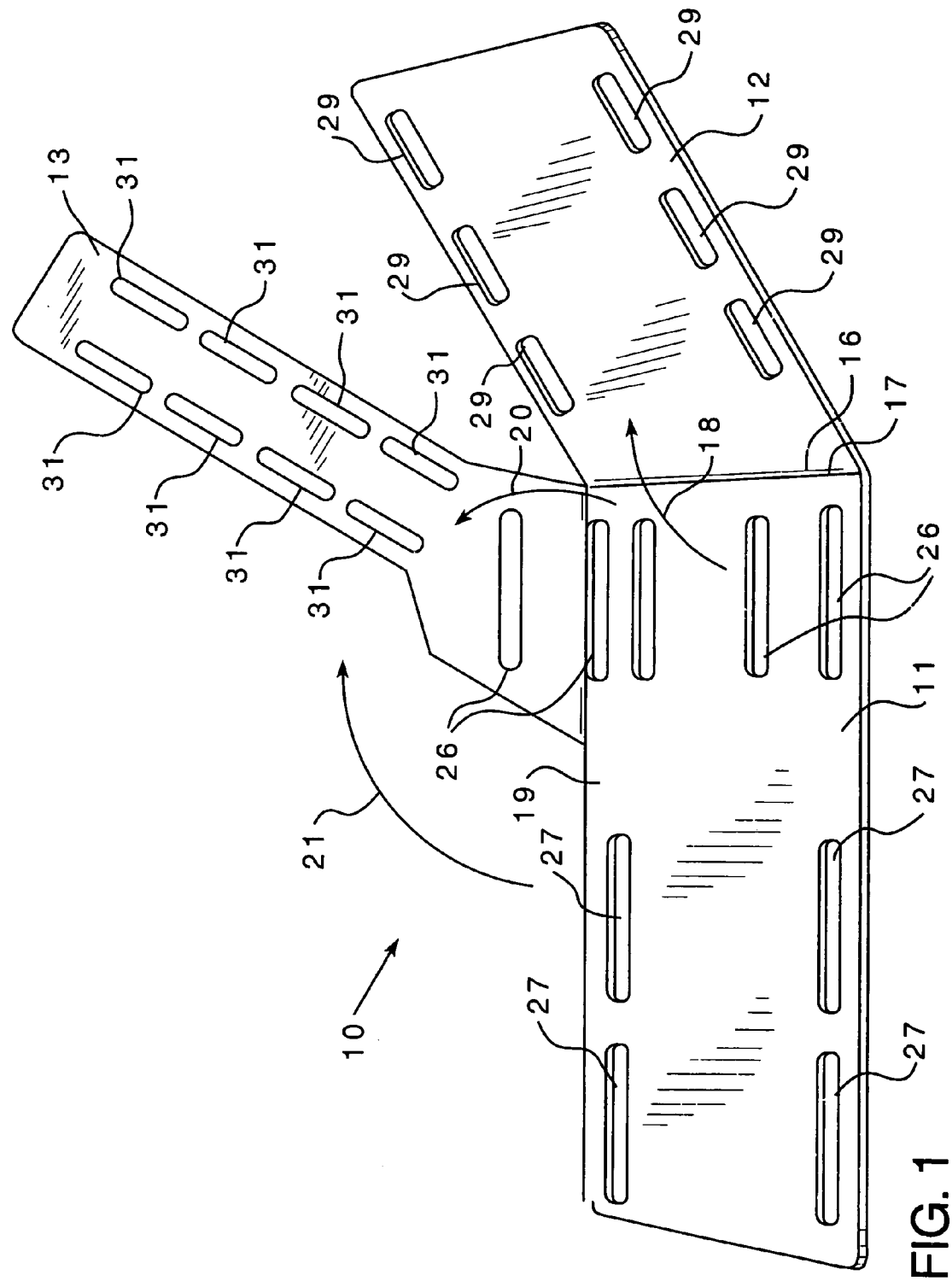
FIG. 1 is a perspective view of one embodiment of the surgical hand support of the present invention without the inclusion of securing straps.
Figure 2:
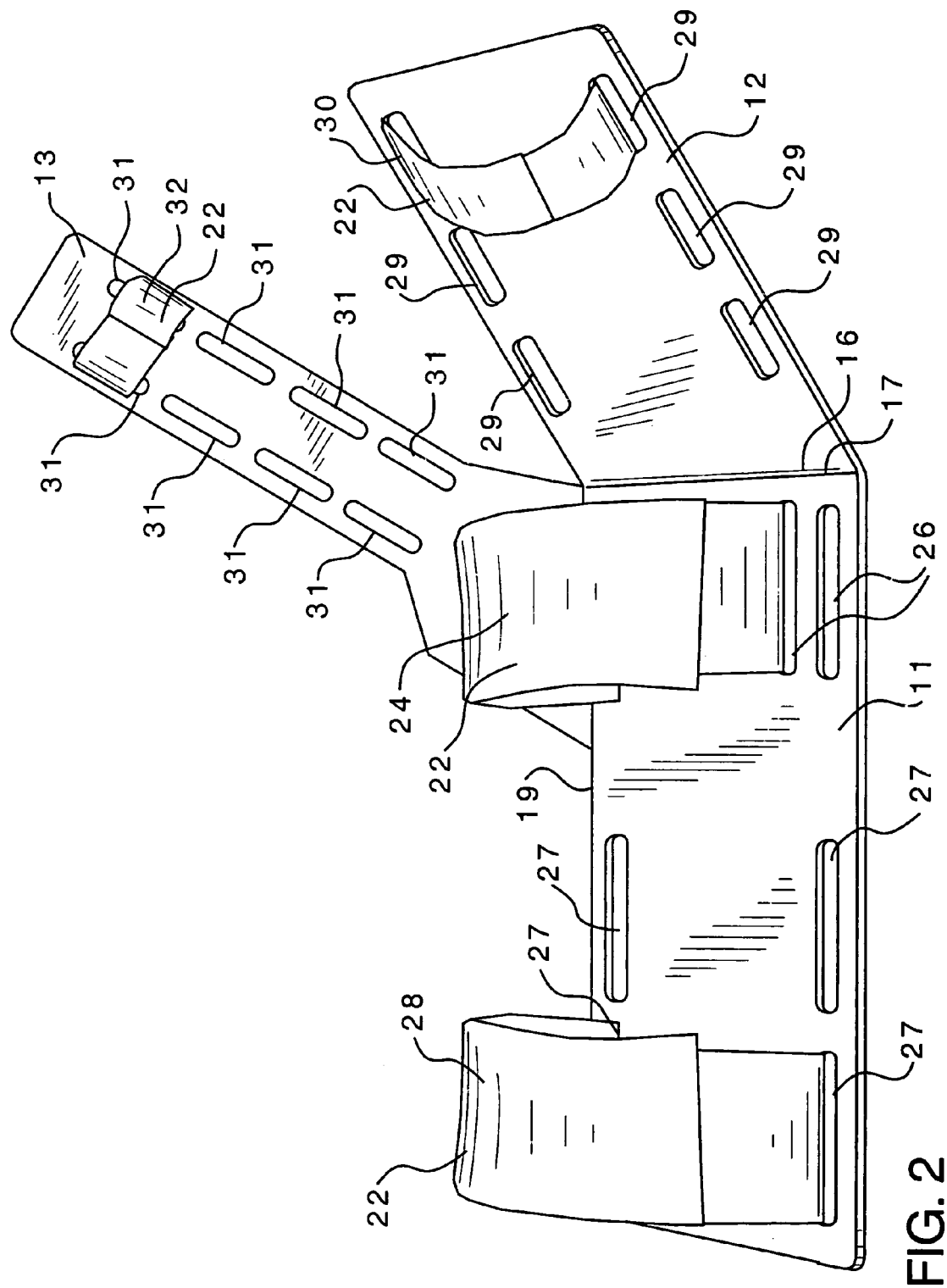
FIG. 2 is a perspective view of the embodiment shown in FIG. 1 with the inclusion of securement straps.
Figure 3:
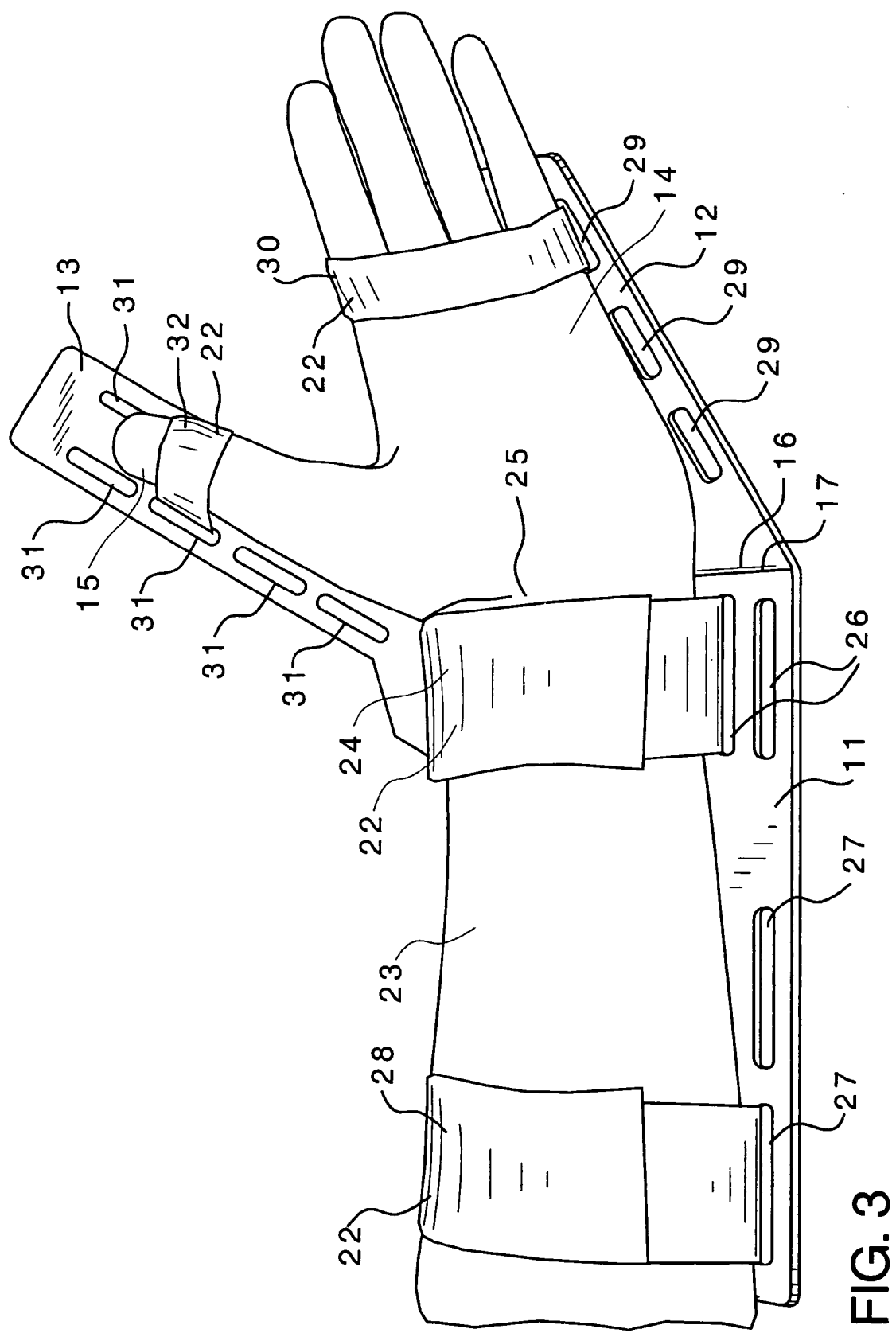
FIG. 3 is a perspective view of the embodiment shown in FIG. 2 with the inclusion of a patient's hand secured thereto.

Referring to the drawings, the surgical hand support 10 of the present invention is rigid and may be constructed of any suitable rigid material such as stainless steel or plastic which can be easily cleaned and sterilized. The rigid support 10 includes an elongate forearm support plate 11 with a hand support plate 12 and a thumb support plate 13 extending from support plate 11. Hand support plate 12 and thumb support plate 13 are respectively dimensioned for engaging the back of an individual's hand 14 and the thumb 15 of the hand 14 as is illustrated in FIG. 3.

The hand support plate 12 extends upwardly from a wrist bend 16 on the forward edge 17 of forearm support plate 11 at an obtuse angle 18, which in this instance is approximately 135°. Thumb support plate 13 extends upwardly from the side edge 19 of forearm support plate 11 adjacent wrist bend 16 at an obtuse angle 20, which in this instance is approximately 120°. Thus the wrist is held in a position of volar flexion. Thumb support plate 13 also extends forward from side edge 19 at an obtuse angle 21, which in this instance is approximately 120°. The angles 18, 20 and 21 of course may be varied within acceptable limits so long as the volar aspect of the thumb 15 is still suitably positioned or presented for surgery and is held in a positon of abduction up and out of the plane of the palm.

Adjustable straps 22 are provided for respectively securely the forearm 23 to forearm plate 11, hand 14 to hand support plate 12 and thumb 15 to thumb support plate 13. Adjustable strap 24 is critically positioned to secure the forearm 23 such that the wrist 25 of hand 14 is retained whereby the hand 14 is bent inwardly at the wrist bend 16. Multiple positioning slots 26 are provided in the support 10 for adjusting wrist strap 24 for securement of wrists of different size.

All of the straps 22 are secured by conventional hook and loop fasteners and each support plate portion of the surgical hand support 10 are provided with multiple slots therealong for adjustment to hands of different size. For example, forearm plate 11 is provided with two sets of strap securement slots 27 so that adjustable strap 28 may be positioned at either slot set depending on the length of the particular forearm. Similarly, hand support plate 12 is provided with multiple sets of strap positioning slots 29 for hand strap 30. Thumb support plate 13 is also provided with multiple sets of strap adjustment slots 31 for thumb strap 32.

The surgical hand support 10 thus holds the thumb 15 in a position which easily allows the surgeon to access and work on the volar side of the thumb particularly at the levels of the distal thenar area, proximal flexion crease, and proximal phalanx portion of the thumb. Most of the common procedures of interest involve these areas. The surgical hand support 10 also maintains the thumb in a stable, secure position so that appropriate manipulation of structures can be safely and easily accomplished without the need for an assistant to provide any manual support to the hand support 10 or the thumb 15.

Typically during an operation on the thumb 15, the patient is placed in the supine position on the main operating table with the hand 14 to be operated upon extending out to the side onto an auxiliary arm table which is secured to the side of the main table. After preparing the arm and hand by cleansing them with sterilizing soaps or solutions, the forearm 23 is draped with sterile drapings such that the hand 14 and arm 23 extend out freely onto the arm table and all of the immediately surrounding areas are covered with sterile sheets with the patient's shoulder and body screened off securely by the sterile sheets. The surgeon then secures the forearm 23, the hand 14, and the thumb 15 to the surgical hand support 10 as illustrated in FIG. 3 using the securing straps 22.

The surgeon generally is seated typically at one side of the arm table. For procedures on the volar side of the thumb, this is typically on the side closest to the patient's lower half, rather than closer to the head of the patient. The surgeon is thus facing the palm side of the thumb as it is being held up by the surgical hand support 10 for appropriate presentation.

The surgical hand support 10 illustrated in the figures is designed for application to the left hand. For the right hand the surgical hand support 10 is constructed with the thumb support plate 13 extending off the opposite side of forearm support plate 11. As an alternative, the surgical hand support 10 may be constructed with thumb support plates 13 extending off both sides of the hand support plate 11 for use as either a left hand or right hand support.

It is also within the realm of the present invention that the respective plates 11, 12 and 13 may be constructed independently and joined with each other by adjustable hinged connections which may be locked at desired angles. Also, the surgical hand support 10 may be manufactured in different sizes, one size to accommodate most adult human hands and a smaller size for children.

I claim:

1. A surgical hand support for positioning a human thumb for performing surgical procedures on the volar side of the thumb, the support comprising:
    a rigid support including an elongate forearm support plate with a hand support plate and a thumb support plate extending from said forearm support plate and dimensioned for respectively engaging the back of an individual's hand and the thumb of said hand;
    said hand support plate extending upwardly from a wrist bend on a forward edge of said forearm support plate at an obtuse angle;
    said thumb support plate extending upwardly from a side edge of said forearm support plate adjacent said wrist bend and at an obtuse angle;
    said thumb support plate also extending forward from said side edge at an obtuse angle;
    adjustable strap means for respectively firmly securing said forearm to said forearm plate, said hand to said hand plate in a position of volar flexion of the wrist and said thumb to said thumb plate in a position of abduction up and out of the plane of the palm whereby the volar side of said thumb is suitably exposed and presented for surgery.

2. The surgical hand support of claim 1 wherein said obtuse upward angle for said hand support plate is approximately 135° and said obtuse upward and forward angles for said thumb support plate are each approximately 120°.

3. The surgical hand support of claim 1 wherein said adjustable strap means includes a strap on said forearm plate positioned for retaining the wrist of said hand bent inwardly at said wrist bend.

4. The surgical hand support of claim 3 wherein said adjustable strap means includes multiple strap positioning slots in said hand and thumb support plates providing multiple selections for positioning securement straps.

5. The surgical hand support of claim 4 wherein said straps are secured with hook and loop fasteners.

* * * * *